(12) United States Patent
Kumar et al.

(10) Patent No.: US 8,987,234 B2
(45) Date of Patent: Mar. 24, 2015

(54) COMPLEX FOR TREATMENT AND/OR PROPHYLAXIS OF PARASITIC INFECTIONS

(75) Inventors: Ashok Kumar, Mumbai (IN); Dharmendra Singh, Mumbai (IN); Pramilkumar Mathur, Mumbai (IN); Vitthal Syryabhan Buchude, Mumbai (IN)

(73) Assignee: IPCA Laboratories Ltd., Mumbai (Maharashtra) (IN)

( * ) Notice: Subject to any disclaimer, the term of this patent is extended or adjusted under 35 U.S.C. 154(b) by 0 days.

(21) Appl. No.: 13/388,729

(22) PCT Filed: Aug. 20, 2010

(86) PCT No.: PCT/IN2010/000554
§ 371 (c)(1), (2), (4) Date: Feb. 3, 2012

(87) PCT Pub. No.: WO2011/021230
PCT Pub. Date: Feb. 24, 2011

(65) Prior Publication Data
US 2012/0136062 A1    May 31, 2012

(30) Foreign Application Priority Data
Aug. 20, 2009 (IN) .......................... 1930/MUM/2009

(51) Int. Cl.
*A01N 37/36* (2006.01)
*C07C 279/26* (2006.01)
*C07C 50/32* (2006.01)

(52) U.S. Cl.
CPC ............... *C07C 279/26* (2013.01); *C07C 50/32* (2013.01)
USPC ........................................................ 514/164

(58) Field of Classification Search
USPC ........................................................ 514/164
See application file for complete search history.

(56) References Cited

U.S. PATENT DOCUMENTS

| | | |
|---|---|---|
| 6,018,080 A | 1/2000 | Dearn |
| 6,166,046 A | 12/2000 | Gutteridge et al. |
| 6,413,993 B1 | 7/2002 | Chulay |
| 6,649,659 B1 | 11/2003 | Dearn |

FOREIGN PATENT DOCUMENTS

| | | |
|---|---|---|
| EP | 123238 A2 | 10/1984 |
| WO | 9412164 A1 | 6/1994 |
| WO | 0061133 A1 | 10/2000 |
| WO | 2009001367 A2 | 12/2008 |
| WO | 2009042960 A1 | 4/2009 |

OTHER PUBLICATIONS

Vippagunta et al 'Crystalline solids' Advanced Drug Delivery Reviews, vol. 48, p. 3-26, 2001.*
Moorthy, Vasee S., et al., "Malaria Vaccine Development", The Lancet, Jan. 2004, pp. 150-156, vol. 363.

* cited by examiner

*Primary Examiner* — Wu-Cheng Winston Shen
*Assistant Examiner* — Christopher R Stone
(74) *Attorney, Agent, or Firm* — Blank Rome LLP (57) ABSTRACT

Disclosed are complexes of an antipneumocystic compound and an antimalarial compound, processes for their preparation, pharmaceutical compositions and methods of using said complexes or compositions for the treatment and/or prophylaxis of parasitic infections.

15 Claims, 4 Drawing Sheets

Figure 1
PXRD

FIGURE 2
FT-IR

Figure 3
DSC

COMPLEX FOR TREATMENT AND/OR PROPHYLAXIS OF PARASITIC INFECTIONS

CROSS-REFERENCE TO RELATED APPLICATIONS

The present application claims the benefit of International Patent Application No. PCT/IN2010/000554, filed Aug. 20, 2010, which in turn claims priority to Indian Patent Application No. 1930/MUM/2009, filed Aug. 20, 2009, the entire disclosures of which are incorporated by reference herein.

TECHNICAL FIELD OF INVENTION

The invention relates to novel complex compounds composed of an antipneumocystic compound and an antimalarial compound, process for their preparation, pharmaceutical compositions and methods of using said complexes for the treatment and/or prophylaxis of parasitic infections.

BACKGROUND OF THE INVENTION

Malaria is an infectious disease that causes severe morbidity and mortality with an estimated 300-500 million cases worldwide and more than 1 million deaths annually in sub-Saharan Africa alone and affected patients are of all age groups. The disease is caused by protozoan parasites of the genus Plasmodium, transmitted by mosquitoes. The most serious forms of malaria are caused by Plasmodium falciparum and Plasmodium vivax, but other species (e.g., Plasmodium ovale, Plasmodium malariae, and Plasmodium knowles[iota]) can also infect humans.

The commonly used drugs are, for example Atovaquone, Proguanil as hydrochloride salt, Primaquine, for the treatment/prophylaxis of malaria.

Atovaquone (Formula I), chemical name being trans-2-[4-(4-chlorophenyl)cyclohexyl]-3-hydroxy-1,4-naphthoquinone, is a hydroxy-1,4-naphthoquinone, an analog of Ubiquinone, with antipneumocystic and anti-malarial activity. It has previously been disclosed, for example, in European Patent No. 1,23,238 that Atovaquone is active (in animals and in vitro) against Pneumocystis (carinii) jirovecii, Plasmodia, and tachyzoite and cyst forms of Toxoplasma gondii.

Formula I

Proguanil (Formula II) as hydrochloride salt is a well-known drug mainly for prophylaxis, but not commonly used for treatment of malaria. Cycloguanil is a metabolite of Proguanil and its formation in vivo has been thought to be responsible for the antimalarial activity of Proguanil. It is one of the safest antimalarial drugs and may be given to young children and pregnant women.

Formula II

Control of malaria has been hampered by the spread of drug resistance in both the Plasmodium parasites and the Anopheles insect vector, and by the lack of an efficacious vaccine (Moorthy, V. S. et al., 2004. Lancet 363:150-156). In order to combat drug resistance and to improve antimalarial chemotherapy, a combination of antimalarials is used, either simultaneously or sequentially. One such combination of Atovaquone and Proguanil as hydrochloride salt (trade name: Malarone) for the treatment of malaria has previously been disclosed in WO9412164, U.S. Pat. No. 6,413,993, WO2009001367, and WO2009042960.

Atovaquone is a highly lipophilic compound with very poor solubility & bioavailability, classified according to the biopharmaceutical classification system (BCS) as class II drug. U.S. Pat. No. 6,018,080 & U.S. Pat. No. 6,649,659 mentions that efficacy of Atovaquone as a therapeutic agent is limited because of its poor bio-availability due to poor solubility of the crystals in common organic/aqueous solvents. It is noted that the label information of Malarone from US FDA shows that absolute bioavailability of the tablet formulation of Atovaquone is only 23%, meaning almost 67% of Atovaquone is not absorbed in the body.

According to European and Indian Pharmacopeia, Proguanil hydrochloride exhibits poor solubility in common organic/aqueous solvents and thus a mere physical admixture composition of these two molecules, like in Malarone, does not alter individual properties and thus the above existing combination exhibits poor solubility and hence less bio-availability.

Therefore, there is a need in the art to improve physico-chemical properties of Atovaquone-Proguanil combination, thereby greatly influencing pharmacokinetic effects, bio-availability and therapeutic efficacy. This forms the object of the present invention.

SUMMARY OF THE INVENTION

Accordingly, the present invention provides novel complex(es) of at least two active principles, Atovaquone and Proguanil, with improved properties that can influence therapeutic efficacy and pharmacokinetic properties. For example, the beneficial physico-chemical properties of the novel complex of the present invention provides a broader therapeutic applicability, a potentiation or synergism of the activity of each of the components of the complex, resulting in the enhancement of pharmacokinetic properties.

In a preferred embodiment, the complexes of the present invention comprises Atovaquone and Proguanil characterized in that the molar ratio of each drug in complex/s is in the range of 1:4 to 4:1, respectively. The complex(es) according to the invention can be well characterized and differentiated from physical mixtures using standard analytical tools analysing differences in physico-chemical properties.

According to another aspect of the present invention, a process for preparation of novel complex(es) is provided. The process comprises contacting Atovaquone and Proguanil in predefined quantities in a suitable medium or carrier and recovering the complex(es) of the present invention from the medium or carrier. In one embodiment of the present invention the process for preparation of complex(es) comprises the steps of: i) forming a solution of each component in an appropriate solvent; ii) mixing said solution of each component, at a suitable temperature; iii) isolating complex of the present invention, for example, by crystallization, evaporating the solvent or by adding a precipitating solvent. Complexes of different molar ratios are obtained by adjusting the molar amounts of each component in step (i).

In an alternate embodiment of the present invention the process comprises suspending or triturating/grinding both components in appropriate molar amounts in a suitable solvent, and then isolating the formed complex by filtration or adding an inert solvent.

In a further aspect, the present invention provides a method for the treatment and/or prophylaxis of a protozoal parasitic infection, e.g. malaria or toxoplasmosis, or an infection caused by *Pneumocystis (carinii) jirovecii* in mammals, including humans, which comprises administering a therapeutically effective amount of complex(es) of the present invention.

In a further aspect, the invention also provides pharmaceutical compositions comprising the complex according to the present invention. The complex according to the invention may be formulated in a therapeutically effective amount into a suitable dosage form such as tablets, capsules, suspensions etc., using known techniques. The dosage forms prepared by the process of the present invention may be administered to a mammal in need, for treatment and/or prophylaxis of parasitic infections by any suitable means.

The details of one or more embodiments of the inventions are set forth in the description below. Other features, objects and advantages of the inventions will be apparent from the appended examples and claims.

DETAILED DESCRIPTION OF THE INVENTION

Unless specified otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described. To describe the invention, certain terms are defined herein specifically as follows:

Unless stated to the contrary, any of the words "including," "includes," "comprising," and "comprises" mean "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth the appended claims.

Unless stated to the contrary, the term 'complex' refers to a structure consisting of a molecule weakly connected to surrounding atom(s) or molecule(s), wherein the molecule(s) or atom(s) are interconnected to each other non-covalently by any connective forces. The term encompasses co-ordination complex, chelate, salt, preferential arrangement of molecules in a crystal, for example, a co-crystal, and any other forms of non-covalent binding between the molecules, thereby said structure exhibits at least one physico-chemical property different from individual components.

The term "isolating" is used to indicate separation or collection or recovery of the compound of the invention being isolated in the specified form. The term "separating from a solvent" with respect to the solids described herein means obtaining a solid of specified characteristics from a solution or a partial solution.

The term "treating" means adding or combining or mixing or grinding the stated reagents or materials to the things being treated. The term "forming a solution" or "solution" means obtaining a solution of a substance in a solvent in any manner. It encompasses partial solutions.

The term 'stable' as used herein, refers to the tendency to remain substantially in the same physical form for at least a month, preferably at least 6 months, more preferably at least a year, still more preferably at least 3 years, when stored under ambient conditions (20° C./60% RH) without external treatment.

The term "patient" whenever referred to herein means mammals including humans. In one aspect of the present invention there is provided novel complexes of antipneumocystic compound and an antimalarial compound. In particular is provided complexes of Atovaquone (Formula I) and Proguanil (Formula II).

The complexes of Atovaquone and Proguanil, according to the present invention are differentiated among each other based on the molar amounts of each component in the complex(es). Each complex according to the invention comprises a molar ratio of Atovaquone to Proguanil in the range of 1:4 to 4:1, respectively. Thus provides complexes of Atovaquone-Proguanil in 1:1 to 1:4 ratios and vice versa, respectively. A particularly preferred complex comprises molar ratio of Atovaquone to Proguanil in the range of 1:1 or 4:1, respectively. More particularly the ratio of Atovaquone to Proguanil is 1:1.

Atovaquone of Formula I may exist as cis or trans isomer, that is to say that the cyclohexyl ring may be cis or trans substituted by the naphthoquinone nucleus and the chlorophenyl group. Both cis and trans isomers and mixtures thereof in any ratio may be used in accordance with the present invention. In general, when the compound is in the form of a mixture of isomers the trans isomer will be present in an amount of about 50% or will be predominant isomer but the mixtures in which the cis isomer predominates can also be used to form the complexes of the present invention. The specific ratio of isomers may be varied as required; typical mixtures include those in which the cis/trans isomer ratio is about 0:100, and 100:0. For use according to the present invention the trans-isomer of the compound of formula (I), or a mixture of its cis or trans isomers containing at least 95% e.g. 99% of the trans isomer, is preferred.

The complexes of the present invention possess entirely different physico-chemical properties compared to individual Atovaquone or Proguanil or its admixture. Thus the complexes of the present invention can be identified and well characterized by methods known in the art per se such as X-Ray Powder Diffraction, Fourier Transform Infrared (FT-IR) spectra, Melting Point etc. It should be understood that operator, instrument and other similar changes may result in some margin of error with respect to analytical characterization of the solid.

The FTIR, DSC and XRPD methods used for the identification and characterization of the novel complex of the present invention are described below:

a) FT-IR spectral analysis

FTIR spectra of novel complex were recorded directly on untreated powder by means of FTIR spectrometer. Spectra was recorded at room temperature from 4000 cm$^{-1}$ to 650 cm$^{-1}$, for each sample 32 scans were collected at a spectral resolution of $4^{cm-1}$.

b) X-ray powder diffraction studies

Analytical characterization of the compound according to the invention was carried out by using X-ray powder diffraction using a PANalytical XpertPRO (PANalytical B.V, Almelo) X-ray powder diffractometer. The X-ray powder diffraction patterns were recorded with Cu K-Alpha1 radiation source (voltage of 45 kV; current: 40 mA). The step scan mode was performed with a step size of 0.008°, at a scan rate of 14.59 s/step.

c) Differential Scanning calorimetry (Abbreviated as DSC)

Differential scanning Calorimetry analysis of the novel complex was recorded at a heating rate of 10° C. per minute at a temperature range from 50° C. to 230° C.

The compound of the invention may be characterized by the positions of the major peaks in the X-ray powder diffractogram (PXRD), but may also be characterized by conventional FT-IR spectroscopy and endotherms in DSC diagram.

Figure 1:
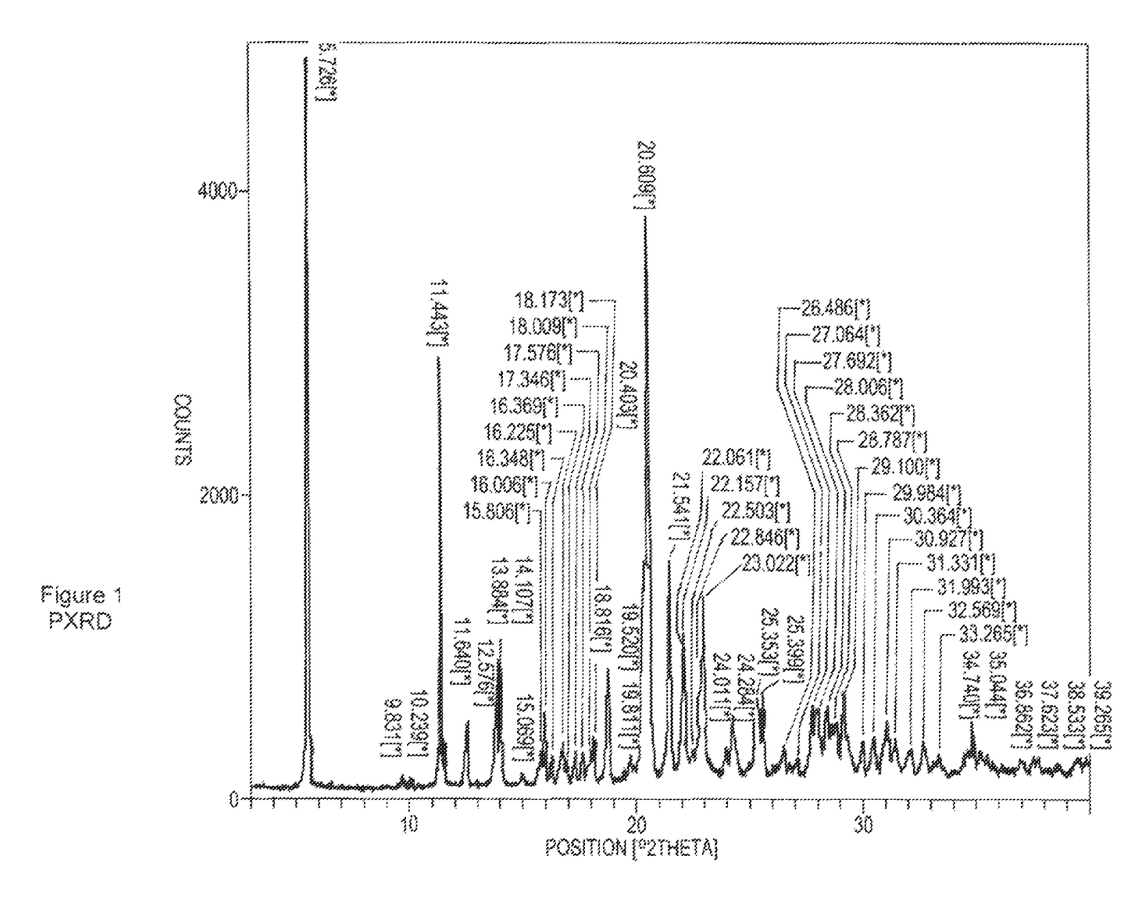
FIG. 1 shows an X-Ray Powder Diffractogram of an exemplary batch of trans-Atovaquone-Proguanil complex in the ratio of 1:1 obtained in accordance with the invention.
Figure 2:
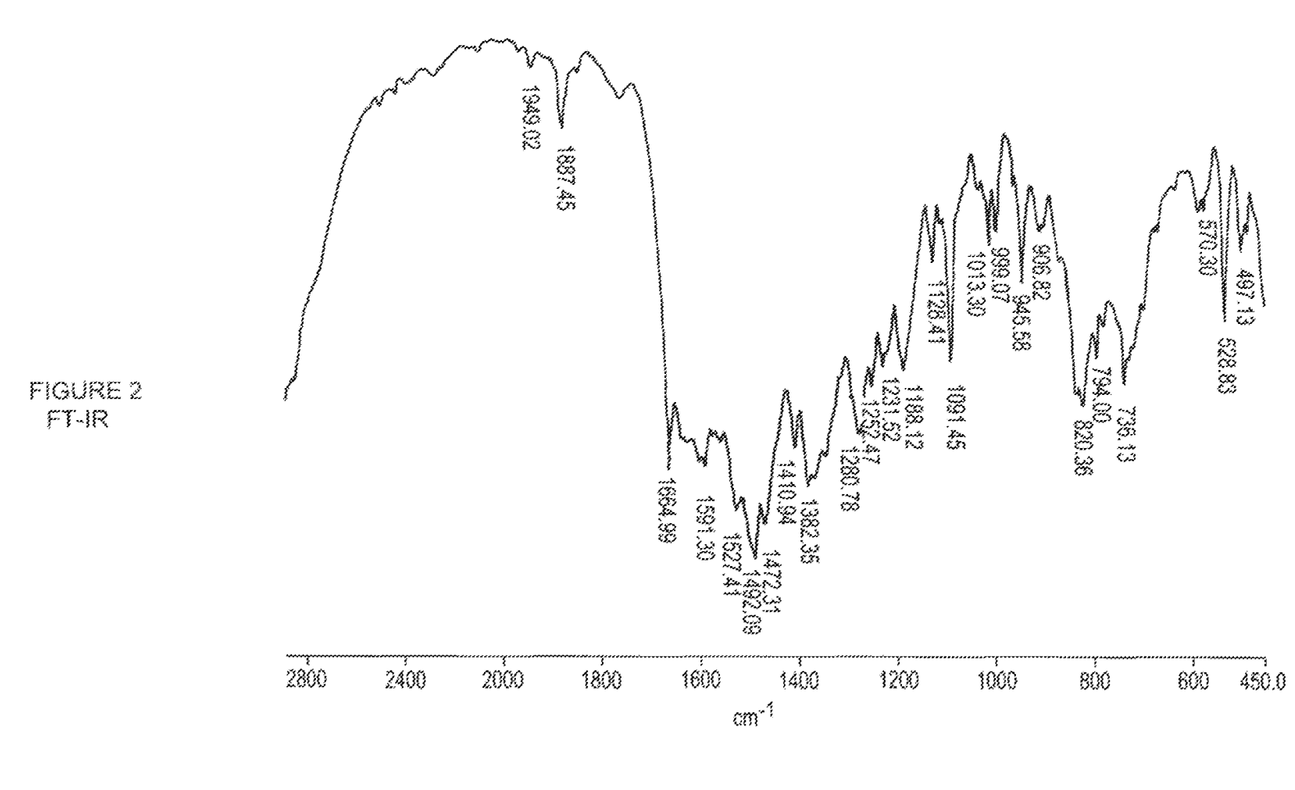
FIG. 2 shows FT Infra-Red spectra of trans-Atovaquone-Proguanil complex in the ratio of 1:1 obtained in accordance with the invention.
Figure 3:
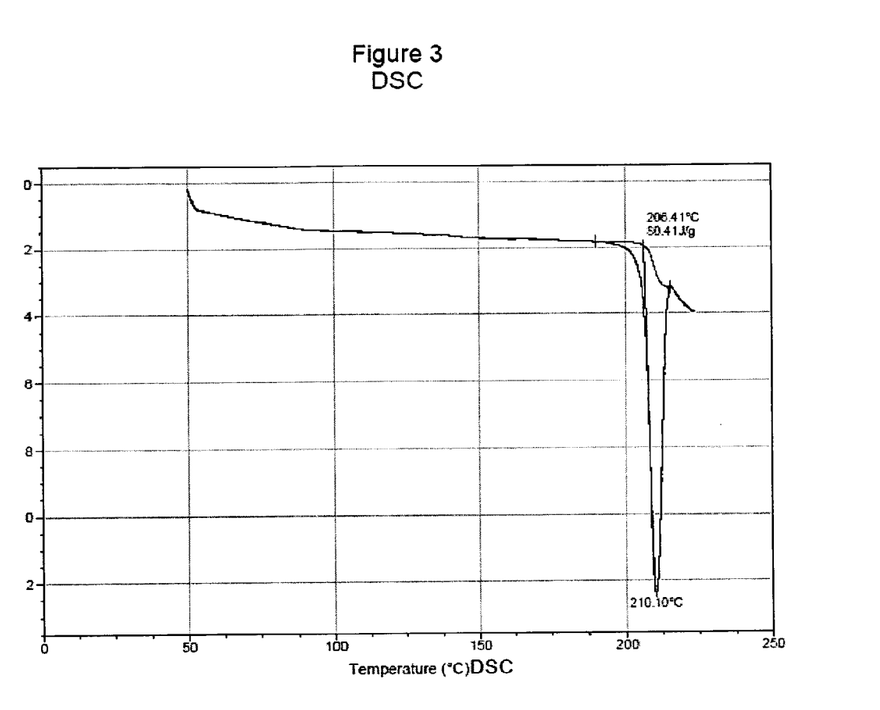
FIG. 3 shows a Differential Scanning calorimetry analysis diagram of an exemplary batch of trans-Atovaquone-Proguanil complex in the ratio of 1:1 obtained in accordance with the invention.
Figure 4:
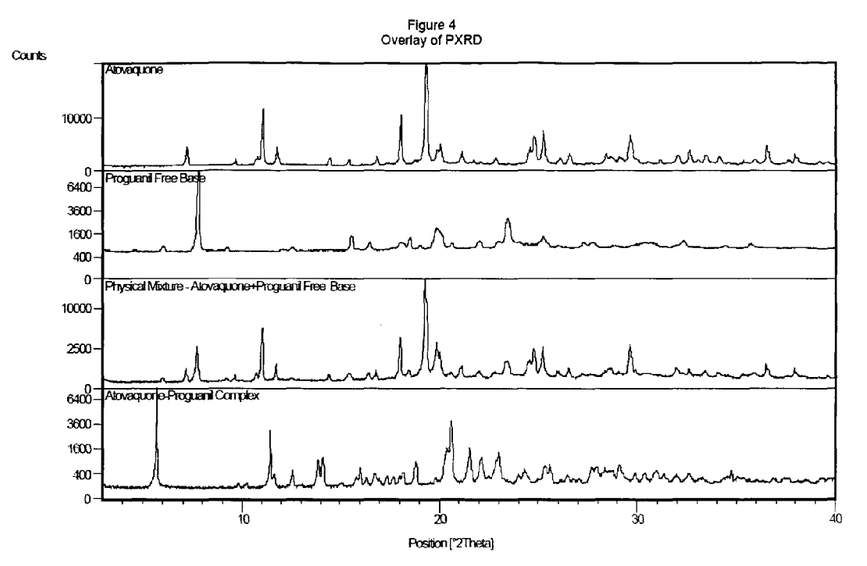
FIG. 4 represents Overlay of PXRD of the complex of the present invention with PXRD patterns of Atovaquone, Proguanil base and a physical admixture of Atovaquone and Proguanil base.

Thus, the character of complex is confirmed either by PXRD patterns, DSC endotherms and FT-IR spectra obtained from a 1:1 complex of Atovaquone-Proguanil, which are provided as FIGS. 1 to 3 respectively. The PXRD pattern shows at least one characteristic and exclusive peak at about 5.72±0.20 degrees 2θ angles. More particularly the PXRD pattern shows characteristic and exclusive peaks at 5.72, 12.56, 13.86, and 14.09±0.20 degrees 2θ angles.

The complex of present invention is further characterized by characteristic absorption in FT-IR spectra at least at wavelength about 3468±3 and 1411±3 cm-$^{1}$. More particularly the complex is characterized by wavelength at about 3468±3, 3343±3, 1668±3, 1411±3 cm-$^{1}$ The complex of present invention is further characterized by endotherms in a DSC. Thermal analysis results in a differential scanning calorimeter thermogram obtained at a heating rate of 10° C. per minute in an open pan that exhibits a single melting endotherm with a peak temperature of about 210° C. The position of the endotherm can shift the position depending upon the heating rate and any contaminations resulting there from.

The main peaks with positions and relative intensities, extracted from the diffractogram in FIG. 1. are given below in table 1. The relative intensities may change from sample to sample or analyses and some additional very weak peaks found in the diffractogram have been omitted from table 1.

TABLE 1

Main peaks with positions and relative intensities, extracted from the diffractogram in FIG. 1

| Sr. No. | 2θ | d-spacing | Relative Intensity [%] |
|---|---|---|---|
| 1 | 5.72 | 15.44 | 100 |
| 2 | 11.43 | 7.73 | 42.87 |
| 3 | 12.56 | 7.04 | 5.86 |
| 4 | 13.86 | 6.38 | 11.91 |
| 5 | 14.09 | 6.28 | 14.53 |
| 6 | 16.31 | 5.43 | 2.72 |
| 7 | 18.79 | 4.72 | 10.61 |
| 8 | 27.94 | 3.19 | 7.68 |

The complex of the present invention shows improved physico-chemical properties, for example, pKa, pH and solubility pattern compared to individual drugs, thus resulting into better pharmaco-kinetic profile.

The 1:1 complex exhibits pKa value of 7.5 whereas pKa value for Atovaquone and Proguanil are 8.39 and 10.64 respectively.

The intrinsic solubility data of complex compound of present invention in 1:1 ratio under standard USP conditions (40% isopropyl alcohol with phosphate buffer pH 8.0), indicates that the solubility of Atovaquone is almost doubled, when compared with that of physical mixture of Atovaquone-Proguanil.

TABLE 2

Intrinsic dissolution profile of Atovaquone and Proguanil from the complex and a 1:1 physical mixture of Atovaquone-Proguanil hydrochloride.

| Time | Atovaquone-Proguanil Complex (1:1) | | Atovaquone-Proguanil hydrochloride physical mixture (1:1) | |
|---|---|---|---|---|
| | % Dissolution Atovaquone | % Dissolution Proguanil | % Dissolution Atovaquone | % Dissolution Proguanil |
| 1 Hrs. | 2.64 | 1.97 | 1.5 | 3.17 |
| 2 Hrs. | 5.61 | 3.64 | 2.54 | 4.11 |
| 3 Hrs. | 7.72 | 5.22 | 3.55 | 5.10 |
| 4 Hrs. | 9.75 | 6.38 | 4.19 | 5.80 |

The above data indicates that the complex of the present invention shows better physico-chemical properties and improved the solubility of poorly soluble Atovaquone in the physical mixture. As a result more Atovaquone gets dissolved from the complex of present invention and made available for simultaneous delivery/absorption in higher proportion in the combination of Atovaquone-Proguanil, resulting in a potentiation or synergism of the activity. So the complex of the present invention can exhibit better pharmacokinetic profile and enhanced bioavailability.

Interestingly, rodent pharmacokinetic profile (in-vivo) of Atovaquone-Proguanil complex is in accordance with the results of intrinsic dissolution studies. Results of comparative rat pharmacokinetic study from an exemplary batch of trans-Atovaquone-Proguanil complex in 1:1 ratio with corresponding ratio of physical mixture have shown that Atovaquone bioavailability is increased by at least two times. The $AUC_{0-inf}$ calculated from PK profile of 1:1 complex of the present invention in comparison with that of Malarone are given in table 2, wherein the complex of the present invention containing only a quarter of the amount of Atovaquone present in physical mixture (Malarone), exhibited higher $AUC_{0-inf}$ levels of Atovaquone as compared to the physical mixture. It shows that the complex of the present invention have significantly higher bioavailability for Atovaquone. So the complex of the present invention exhibits better therapeutic profile than physical mixture.

TABLE 3

$AUC_{0-inf}$ of Atovaquone calculated from Rat PK profile of trans-Atovaquone-Proguanil complex (1:1) and a physical mixture (Malarone).

| S. No. | Sample | Atovaquone Dose | $AUC_{0-inf}$ (ng/hr × mL) |
|---|---|---|---|
| 1. | Complex (1:1) | 6.166 mg/kg | 298501.894 ± 117805.568 |
| 2. | Physical Mixture (Malarone) | 26.011 mg/kg | 223163.826 ± 64461.432 |

In a further aspect, the present invention provides processes for the preparation of the complex(es). The process comprises contacting Atovaquone and Proguanil in pre-defined quantities in a suitable medium or carrier and recovering the complex(es) of the present invention from the medium or carrier. In one embodiment, the process comprises; i) forming a solution of each components in an appropriate molar amounts in one or more solvents; ii) mixing said solution at a suitable temperature and iii) isolating the complex from said solution.

In a preferred embodiment, preparation of complex of the present invention comprises; i) forming a solution of Atovaquone, or isomers thereof, in an appropriate solvent; ii) adding said solution to a solution of Proguanil in an appropriate solvent, at a suitable temperature and stirring for a suitable time; iii) isolating the complex. Alternately at stage ii) the solution of Proguanil may also be added to solution of Atovaquone or isomers thereof. The solvent used for the dissolution of Atovaquone and Proguanil may be either same or different.

In an alternate embodiment of the present invention the process comprises suspending or triturating both components in appropriate molar amounts in presence of a suitable solvent, and then isolating the formed complex by filtration or adding an inert solvent. The complex of the present invention is optionally purified in inert solvent.

In the process, the molar ratios of Atovaquone and Proguanil are altered to form different complexes each having different molar amounts. The complex formation reaction may be carried out at a temperature ranging from ambient to reflux temperature of the solvent, though lower temperature can be used.

As used herein, the expression "reaction solvent", "inert solvent", "precipitating solvent" and "appropriate solvent" refer to a solvent or mixture of solvents which does not interact with starting materials, reagents, intermediates or products in a manner which adversely affects the yield and quality of the desired product.

The inert or appropriate solvent may be selected from, but not limited to, a ketone like acetone, methyl ethyl ketone, or methyl propyl ketone, a halogenated hydrocarbon like chloroform, ethylenedichloride, or methylenechloride; an ester like ethylacetate; C1-4 alcohol, like methanol, ethanol, propanol, butanol; or mixtures thereof. The less polar solvent may be selected from, but not limited to, hydrocarbon like hexane, heptane, toluene; or mixtures thereof. The amount of solvent is not crucial and will depend on the process conversion & conditions desired.

The reaction mixture is stirred vigorously at suitable temperature. By a suitable temperature is meant a temperature at which the solution can be formed and be able to induce the transformation of Atovaquone and Proguanil into the novel complex. Examples of such suitable temperatures include, but are not limited to, room temperature to reflux temperature of the reaction media.

By a suitable time is meant a time that results in complete conversion of the starting material into novel complex without causing any decomposition of either compounds, i.e. results in a good yield. This suitable time can be established by routine experimentation.

The isolation of the complex is accomplished by conventional techniques such as crystallization, evaporation, adding a precipitating solvent etc. In a preferred embodiment crystallization is accomplished either by evaporation of reaction solvent or by the addition of less polar solvents to afford the complex according to the present invention. The complex is isolated at an ambient temperature, preferably lower than room temperature, still preferably less than 15° C. and more preferably at 0-5° C.

In a further aspect, the present invention provides a method for the treatment and/or prophylaxis of a protozoal parasitic infection, e.g. malaria or toxoplasmosis, or an infection caused by *Pneumocystis (carinii) jirovecii* in mammals, including humans, which comprises administering a therapeutically effective amount of complex(es) of the present invention.

In a further aspect, the present invention provides a method of reducing protozoal count in infected blood of a mammal, which comprises administering a therapeutically effective amount of complex(es) of the present invention.

In another aspect, the invention provides a method of using a therapeutically effective amount of the complex according to the present invention for the prevention, control and treatment of diseases or disorders of a protozoal parasitic infection, e.g. malaria or toxoplasmosis, or an infection caused by *Pneumocystis (carinii) jirovecii* in mammals, including humans.

In a further aspect, the invention provides use of Atovaquone-Proguanil complex according to the present invention for the preparation of medicament useful for the treatment or prophylaxis or both of a protozoal parasitic infection or an infection caused by *Pneumocystis (carinii) jirovecii* in mammals.

In a further aspect, the invention also provides pharmaceutical compositions comprising a complex according to the present invention. The complex according to the invention may be formulated in a therapeutically effective amount, optionally together with a pharmaceutical acceptable agent/carrier/excipients, for example with an inorganic or organic, solid or optionally liquid pharmaceutically acceptable carrier, into a suitable dosage form such as tablets, capsules, pills, granules, powders, emulsions, suspensions, syrups, pellets etc., using known techniques. Such agents/carriers/excipients may be selected from, but not limited to, cellulose, hydroxypropyl cellulose; hydroxypropyl methyl cellulose, lactose, starch, sodium starch glycollate, povidone-K30, magnesium stearate, magnesium aluminum silicate, sodium saccharin, titanium dioxide and polyethylene glycol.

The dosage forms prepared by the process of the present invention may be administered to a mammal in need, for treatment and/or prophylaxis of protozoal parasitic infections e.g. malaria or toxoplasmosis, or an infection caused by *Pneumocystis (carinii) jirovecii*. Pharmaceutical formulations include those suitable for oral, nasal, topical (including dermal, buccal and sublingual), rectal and parenteral (including subcutaneous, intradermal, intramuscular and intravenous), administration as well as administration by nasogastric tube. The formulation may, where appropriate, be conventionally presented in discrete dosage units and may be prepared by any of the methods well known in the art of pharmacy. All methods include the step of bringing into association the active ingredients with liquid carriers or finely divided solid carriers or both and then, if necessary, shaping the product into the desired formulation.

The amount of a complex of the present invention required to be effective as an antiparasitic agent will, of course, vary and is ultimately at the discretion of the medical or veterinary practitioner. The factors to be considered include the route of administration and nature of the formulation, the mammal's body weight, age and general condition and the nature and severity of the disease to be treated. In general, a suitable effective dose of the complex of present invention for administration to human for treatment of malaria is in the range of 1 to 20 mg/kg/day, preferably from 1.3 to 15 mg/kg/day of the complex, more preferably from 1.4 to 12.5 mg/kg/day of the complex.

A suitable effective dose of the complex of present invention for administration to human for prophylaxis of malaria is in the range of 1 to 4.5 mg/kg/day, preferably from 1.3 to 3.5 mg/kg/day of the complex, more preferably 1.4 to 3 mg/kg/day of the complex.

Additionally the complex(es) according to the invention occurs as a solvate e.g. a hydrate. Said solvates and hydrates are also within the scope of this invention.

The complex(es) according to the invention exist in a form selected from the group consisting of a crystalline form, partly crystalline form and polymorphous form. The complex(es) according to the invention exist also in amorphous form.

The examples provided below are illustrative and are not intended to limit the scope of the claimed invention.

EXAMPLES

Synthesis and Purification

Example—1

Trans-Atovaquone 3.0 gm (0.00818 mole) was dissolved in 120 ml methylenedichloride and 24 ml methanol. To this was added drop-wise a solution of 2.07 gm (0.00818 mole) Proguanil in 24 ml methylenedichloride and 6 ml methanol, mixture refluxed, methylenedichloride was distilled out, 10 ml hexane added and cooled to 0-5° C. Filtered, washed with hexane, and dried at 60-65° C. to yield 5.0 gm.
Purification 3.9 gm of the product obtained above was taken in 40 ml methanol and 20 ml methylenedichloride, heated to reflux, and methylenedichloride distilled out. Added 10 ml hexane, filtered, washed with hexane, and dried at 60-65° C. Yield 3.6 gm (92.3%). The XRPD, IR spectra & DSC of the sample were recorded and are reproduced in FIGS. 1 to 3.

Example—2

To Atovaquone 1.0 gm (0.00272 mole) in 60 ml chloroform was added 0.692 gm (0.00272 mole) Proguanil in 10 ml methanol drop wise and the reaction mass was refluxed. Solvent was distilled out, 20 ml hexane and 3 ml methanol added and filtered, washed with hexane. Dried at 60-65° C. Yield 1.5 gm (88.7%).

Example—3

To Atovaquone 1.0 gm (0.00272 mole) dissolved in 80 ml acetone was added 0.692 gm (0.00272 mole) Proguanil dissolved in 10 ml methanol, refluxed the mass and solvent was distilled out. Yield 1.5 gm (88.7%)

Example—4

Atovaquone 1.0 gm (0.00272 mole) was dissolved in 60 ml ethyl acetate, to this 0.692 gm (0.00272 mole) Proguanil dissolved in 10 ml methanol was added drop wise, refluxed. Solvent was distilled out, 20 ml hexane and 3 ml methanol added and solids filtered, washed with hexane, dried at 60-65° C. Yield 1.5 gm (88.7%).

Example—5

Atovaquone 0.6 gm (0.001637 mole) was mixed with 0.415 gm (0.001637 mole) of Proguanil and homogenised by grinding in pastel and mortar, methanol was added to it, filtered and washed with hexane, dried at 60-65° C. Yield 1.0 gm (98.56%).

Example—6

To Atovaquone 1.0 gm (0.00272 mole) slurried in 10 ml methylenedichloride was added 0.692 gm (0.00272 mole) Proguanil in 5 ml methylenedichloride, refluxed, solvent was distilled out, and 20 ml hexane added. The solids filtered, washed with hexane, and dried at 60-65° C. Yield 1.5 gm (88.7%).

Example—7

1.0 gm Atovaquone (0.00272 mole) was dissolved in 40 ml methylenedichloride and 10 ml methanol. To this 0.172 gm Proguanil (0.000678 mole) dissolved in 8 ml methylenedichloride and 2 ml methanol was added drop wise and refluxed. Methylene chloride was distilled out, contents cooled to 30±2° C., filtered, washed with hexane, and dried the product at 60-65° C. Yield 0.8 gm Example—8

Trans-Atovaquone 1 kg was dissolved in 40 liters of methylenedichloride and 8 liters of methanol. To this was added solution of 0.69 kg of Proguanil in 8.0 liters of methylenedichloride and 2 liters of methanol drop wise, refluxed, methylenedichloride was distilled out, 3.3 liters of hexane added and cooled to 0-5° C. Filtered, washed with hexane, dried at 60-65° C. to yield 1.67 kg.
Pharmaceutical Compositions The following examples illustrate conventional pharmaceutical compositions which may be employed in accordance with the present invention:

Example—1

| Film coated tablet | |
|---|---|
| Core: | |
| Complex of Example I | 211 mg |
| (Atovaquone - 125 mg) | |
| (Proguanil - 86 mg) | |
| Microcrystalline cellulose (Avicel PH 101) | q.s. |
| Hydroxypropyl cellulose, Lo-sub, (LHPC, LHII) | q.s. |

| Film coated tablet | |
| --- | --- |
| Sodium starch glycollate (Explotab) | q.s. |
| Povidone K30 | q.s. |
| Magnesium Stearate | q.s. |
| Compression weight | 288 mg |
| Coating: | |
| Polymer dispersion (Hydroxypropylmethyl cellulose and titanium dioxide and polyethylene glycol 400 and colourant) Polishing: | 10 mg |
| Polyethylene glycol 8000 | 2 mg |
| Total weight | 300 mg |

Example—2

| Dispersible film coated tablet | |
| --- | --- |
| Core: | |
| Complex of Example I (Atovaquone - 125 mg) (Proguanil - 86 mg) | 211 mg |
| Microcrystalline cellulose (Avicel PH 101) | q.s. |
| Hydroxypropyl cellulose, Lo-sub, (LHPC, LHII) | q.s. |
| Sodium starch glycollate (Explotab) | q.s. |
| Povidone K30 | q.s. |
| Magnesium Stearate | q.s. |
| Magnesium aluminium silicate (Veegum F) | q.s. |
| Sodium saccharin | q.s. |
| Compression weight | 288 mg |

| Dispersible film coated tablet | |
| --- | --- |
| Coating: | |
| Polymer dispersion (Hydroxypropylmethyl cellulose and titanium dioxide and polyethylene glycol 400 and colourant) Polishing: | 10 mg |
| Polyethylene glycol 8000 | 2 mg |
| Total weight | 300 mg |

Biological Test Results

Example—1

Comparative pharmacokinetic study of complex of example-I at two doses with physical mixtures of Atovaquone and Proguanil hydrochloride (Malarone) was carried for profiling of bioavailability of Atovaquone, Proguanil and Cycloguanil from all three samples. Four groups of 13-14 weeks old five albino Wistar rats were made through random selection. Group I served as a vehicle control and received only 0.5% sodium carboxymethyl cellulose, group II and group III received two different doses of complex of Example I, and group IV received a physical mixture of Atovaquone and Proguanil hydrochloride (Malarone). The dose volume used for this study was 10 ml/Kg of body weight. Orbital sinus was used as blood collection site and the blood was collected in EDTA coated microcentrifuge tubes at different time points between 0 min (pre dose) to 240 hrs. Plasma samples were analyzed by LC MS/MS. Comparative pharmacokinetic profiles of Atovaquone, Proguanil and Cycloguanil are as given below in table 3, 4, and 5 respectively:

TABLE 4

Comparative rat pharmacokinetic profile of Atovaquone from complex of example-I, physical mixture (1:1) and physical mixture (Malarone).

| Group | Atovaquone dose (mg/kg) | $C_{max}$ (ng/ml) | $T_{max}$ (hr) | $T_{1/2}$ (hr) | $AUC_{0-inf}$ (ng/hrxml) | $V_d$ (L/Kg) | Cl (L/kg/hr) | MRT (hr) |
| --- | --- | --- | --- | --- | --- | --- | --- | --- |
| Control | — | N.D. | N.D. | N.D. | N.D. | N.D. | N.D. | N.D. |
| Complex | 13.005 | 6779.226 ± 1212.761 | 12.8 ± 6.573 | 29.542 ± 4.583 | 472148.864 ± 60492.192 | 0.001 ± 0.000 | 0.000 ± 0.000 | 50.644 ± 6.145 |
| Complex | 6.166 | 4925.009 ± 1232.578 | 19.200 ± 6.573 | 26.833 ± 2.145 | 298501.894 ± 117805.568 | 0.001 ± 0.000 | 0.000 ± 0.000 | 39.240 ± 4.849 |
| Physical Mixture (Malarone) | 26.001 | 4174.482 ± 821.830 | 9.7 ± 9.080 | 29.859 ± 3.808 | 223163.826 ± 64461.432 | 0.005 ± 0.001 | 0.000 ± 0.000 | 39.977 ± 3.806 |

* N.D.—Not Detectable

TABLE 5

Comparative rat pharmacokinetic profile of Proguanil from complex of example-I, physical mixture (1:1) and physical mixture (Malarone).

| Group | Proguanil dose (mg/kg) | $C_{max}$ (ng/ml) | $T_{max}$ (hr) | $T_{1/2}$ (hr) | $AUC_{0-inf}$ (ng/hrxml) | $V_d$ (L/Kg) | Cl (L/kg/hr) | MRT (hr) |
| --- | --- | --- | --- | --- | --- | --- | --- | --- |
| Control | — | 2.462 ± 2.776 | 5.200 ± 6.211 | N.D. | N.D. | N.D. | N.D. | 6.712 ± 5.511 |
| Complex | 8.995 | 94.515 ± 30.475 | 1.15 ± 0.822 | 13.149 ± 9.920 | 485.239 ± 92.796 | 0.349 ± 0.227 | 0.019 ± 0.003 | 4.933 ± 0.43 |
| Complex | 4.2642 | 87.400 ± 20.224 | 2.800 ± 1.095 | 4.779 ± 1.554 | 497.306 ± 130.069 | 0.061 ± 0.017 | 0.009 ± 0.003 | 5.581 ± 0.865 |

TABLE 5-continued

Comparative rat pharmacokinetic profile of Proguanil from complex of example-I, physical mixture (1:1) and physical mixture (Malarone).

| Group | Proguanil dose (mg/kg) | $C_{max}$ (ng/ml) | $T_{max}$ (hr) | $T_{1/2}$ (hr) | $AUC_{0-inf}$ (ng/hrxml) | $V_d$ (L/Kg) | Cl (L/kg/hr) | MRT (hr) |
|---|---|---|---|---|---|---|---|---|
| Physical Mixture (Malarone) | 10.400 | 139.325 ± 219.112 | 0.65 ± 0.762 | 7.521 ± 4.352 | 194.476 ± 76.866 | 0.675 ± 0.450 | 0.059 ± 0.016 | 4.567 ± 1.788 |

\* N.D.—Not Detectable

TABLE 6

Comparative rat pharmacokinetic profile of Cycloguanil from complex of example-I, physical mixture (1:1) and physical mixture (Malarone).

| Group | Proguanil dose (mg/kg) | $C_{max}$ (ng/ml) | $T_{max}$ (hr) | $T_{1/2}$ (hr) | $AUC_{0-inf}$ (ng/hrxml) | $V_d$ (L/Kg) | Cl (L/kg/hr) | MRT (hr) |
|---|---|---|---|---|---|---|---|---|
| Control | — | 0.419 ± 0.936 | 12.000 ± N.D. | N.D. | N.D. | N.D. | N.D. | 12.000 ± N.D. |
| Complex | 8.995 | 6.954 ± 1.367 | 2.00 ± 0.000 | 4.406 ± 2.239 | 34.797 ± 3.868 | 1.618 ± 0.760 | 0.261 ± 0.026 | 5.106 ± 1.631 |
| Complex | 4.2642 | 4.667 ± 0.875 | 3.200 ± 1.095 | 5.620 ± 2.332 | 38.910 ± 11.333 | 0.873 ± 0.230 | 0.118 ± 0.036 | 5.753 ± 2.070 |
| Physical Mixture (Malarone) | 10.400 | 1.47 ± 0.657 | 2.8 ± 1.095 | 2.666 ± N.D. | 13.992 ± N.D. | 2.86 ± N.D. | 0.744 ± N.D. | 2.991 ± 0.463 |

\* N.D.—Not Detectable

The results of this comparative pharmacokinetic study show that the bioavailability of Atovaquone from the complex is increased by at least four times as compared with Malarone. Overall the complex of the present invention exhibits better pharmacokinetic profile than the physical mixtures and the bioavailability of Atovaquone is significantly increased.

We claim:

1. An atovaquone-proguanil complex characterized by:
a powder X-ray diffraction pattern with characteristic peaks at about 5.72, 12.56, 13.86 and 14.09±0.20 degrees two-theta.

2. The complex according to claim 1, wherein the molar ratio of atovaquone to proguanil in complex is in the range of 1:4 to 4:1.

3. The complex according to claim 1, wherein the molar ratio of atovaquone to proguanil in complex is 1:1.

4. The complex according to claim 1, wherein the complex exists in a form selected from the group consisting of crystalline, partly crystalline, polymorphous, amorphous, and solvates thereof.

5. The complex according to claim 1, wherein the atovaquone has a ratio of cis to trans isomer in the range of 0:100 to 100:0.

6. The complex according to claim 1, wherein the trans-atovaquone to proguanil molar ratio is 1:1.

7. The complex according claim 1, further characterized by a differential scanning calorimetric thermogram having an endothermic peak at about 210° C.

8. The complex according to claim 1, further characterized by an FTIR spectrum with peaks at about 1665, 1091, 820 and 528 cm$^{-1}$.

9. A pharmaceutical composition comprising the atovaquone-proguanil complex of claim 1.

10. The composition of claim 9, further comprising a pharmaceutically acceptable excipient.

11. The composition of claim 9, in a dosage form suitable for oral, rectal, nasal, topical, or parenteral administration.

12. A method for treating a protozoal parasitic infection comprising the step of administering a therapeutically effective amount of the atovaquone-proguanil complex of claim 1.

13. The method of claim 12, wherein the protozoal parasitic infection is malaria or toxoplasmosis.

14. A method for treating an infection caused by *Pneumocystis* (*carinii*) *jirovecii* in mammals comprising the step of administering a therapeutically effective amount of the atovaquone-proguanil complex of claim 1.

15. A method for reducing protozoal count, the method comprising the step of administering a therapeutically effective amount of the atovaquone-proguanil complex of claim 1.

\* \* \* \* \*